(12) United States Patent
Iyoku

(10) Patent No.: US 10,786,440 B2
(45) Date of Patent: Sep. 29, 2020

(54) WATER ABSORBING RESIN HAVING SILOXANE SKELETON AND COSMETIC CONTAINING THE SAME

(71) Applicant: SHIN-ETSU CHEMICAL CO., LTD., Tokyo (JP)

(72) Inventor: Hiroomi Iyoku, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/070,589

(22) PCT Filed: Dec. 13, 2016

(86) PCT No.: PCT/JP2016/005112
§ 371 (c)(1),
(2) Date: Jul. 17, 2018

(87) PCT Pub. No.: WO2017/130257
PCT Pub. Date: Aug. 3, 2017

(65) Prior Publication Data
US 2019/0021982 A1 Jan. 24, 2019

(30) Foreign Application Priority Data

Jan. 29, 2016 (JP) .................. 2016-015975

(51) Int. Cl.
| | |
|---|---|
| *A61K 8/895* | (2006.01) |
| *A61Q 15/00* | (2006.01) |
| *A61Q 17/04* | (2006.01) |
| *A61Q 19/00* | (2006.01) |
| *A61K 8/06* | (2006.01) |
| *C08F 220/00* | (2006.01) |
| *C08F 299/06* | (2006.01) |
| *A61Q 5/02* | (2006.01) |

(52) U.S. Cl.
CPC ............... *A61K 8/895* (2013.01); *A61K 8/06* (2013.01); *A61Q 5/02* (2013.01); *A61Q 15/00* (2013.01); *A61Q 17/04* (2013.01); *A61Q 19/00* (2013.01); *C08F 220/00* (2013.01); *C08F 299/06* (2013.01)

(58) Field of Classification Search
CPC .............................. A61K 8/895; C08F 220/00
See application file for complete search history.

(56) References Cited

U.S. PATENT DOCUMENTS

| | | | |
|---|---|---|---|
| 4,698,178 A | 10/1987 | Huttinger et al. | |
| 4,769,431 A | 9/1988 | Ratkowski | |
| 4,970,252 A | 11/1990 | Sakuta et al. | |
| 4,987,169 A | 1/1991 | Kuwata et al. | |
| 5,118,764 A | 6/1992 | Ichinohe et al. | |
| 5,236,986 A | 8/1993 | Sakuta | |
| 5,538,793 A | 7/1996 | Inokuchi et al. | |
| 6,616,920 B1 | 9/2003 | Ito et al. | |
| 2002/0131947 A1 | 9/2002 | Nakanishi | |

(Continued)

FOREIGN PATENT DOCUMENTS

| | | |
|---|---|---|
| CN | 1938000 A | 3/2007 |
| EP | 0184924 A2 | 6/1986 |

(Continued)

OTHER PUBLICATIONS

Jul. 3, 2019 Extended Search Report issued in European Application No. 16887846.0.

(Continued)

*Primary Examiner* — Andrew S Rosenthal
(74) *Attorney, Agent, or Firm* — Oliff PLC

(57) ABSTRACT

A water absorbing resin has a siloxane skeleton which is a copolymer containing a structural unit derived from a polymerizable vinyl monomer (A) shown by the general formula (1), a structural unit derived from a polymerizable vinyl monomer (B) shown by the general formula (3), and a structural unit derived from an organopolysiloxane (C) having polymerizable groups at the both terminals thereof shown by the general formula (4). The water absorbing resin has a siloxane skeleton that is capable of thickening an aqueous composition without making it sticky, together with a cosmetic containing the same.

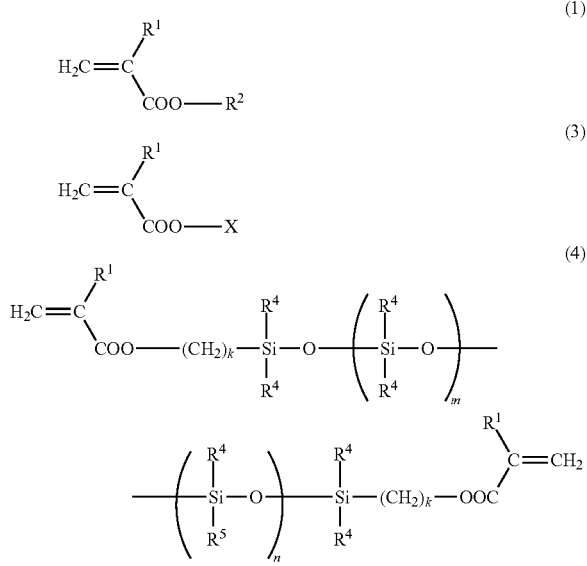

22 Claims, No Drawings

(56) References Cited

U.S. PATENT DOCUMENTS

| | | |
|---|---|---|
| 2003/0199660 A1 | 10/2003 | Sakuta |
| 2004/0234477 A1 | 11/2004 | Sakuta |
| 2004/0253197 A1 | 12/2004 | Sakuta |
| 2007/0196291 A1 | 8/2007 | Sakuta |
| 2008/0064786 A1* | 3/2008 | Tanaka ............... C09D 11/322 523/201 |
| 2008/0175809 A1 | 7/2008 | Sakuta et al. |
| 2014/0066540 A1 | 3/2014 | Ueyama et al. |

FOREIGN PATENT DOCUMENTS

| | | | |
|---|---|---|---|
| EP | 1736138 A1 | 12/2006 | |
| EP | 1946799 A2 * | 7/2008 | ............ A61K 8/895 |
| EP | 1946799 A2 | 7/2008 | |
| JP | S61-90732 A | 5/1986 | |
| JP | S62-34039 B2 | 7/1987 | |
| JP | H03-047848 A | 2/1991 | |
| JP | H03-093834 A | 4/1991 | |
| JP | H06-055897 B2 | 7/1994 | |
| JP | H06-060286 B2 | 8/1994 | |
| JP | H07-196815 A | 8/1995 | |
| JP | H07-239458 A | 9/1995 | |
| JP | H07-91389 B2 | 10/1995 | |
| JP | H07-330907 A | 12/1995 | |
| JP | H08-133926 A | 5/1996 | |
| JP | H09-59386 A | 3/1997 | |
| JP | 2613124 B2 | 5/1997 | |
| JP | H09-136813 A | 5/1997 | |
| JP | 2631772 B2 | 7/1997 | |
| JP | 2844453 B2 | 1/1999 | |
| JP | 2001-131248 A | 5/2001 | |
| JP | 2001-342255 A | 12/2001 | |
| JP | 2002-179798 A | 6/2002 | |
| JP | 2002-293969 A | 10/2002 | |
| JP | 2006-282599 A | 10/2006 | |
| JP | 2015-528586 A | 9/2015 | |
| WO | 03/020828 A1 | 3/2003 | |
| WO | 03/024413 A1 | 3/2003 | |
| WO | WO-2014033442 A1 * | 3/2014 | |

OTHER PUBLICATIONS

Jan. 4, 2019 Office Action issued in Japanese Patent Application No. 2016-015975.

Jul. 31, 2018 International Preliminary Report on Patentability issued in International Patent Application No. PCT/JP2016/005112.

Feb. 7, 2017 International Search Report issused in International Application No. PCT/JP2016/005112.

Feb. 3, 2020 Office Action issued in Chinese Patent Application No. 201680080307.4.

Jun. 24, 2020 Office Action issued in European Patent Application No. 16 887 846.0.

* cited by examiner

WATER ABSORBING RESIN HAVING SILOXANE SKELETON AND COSMETIC CONTAINING THE SAME

TECHNICAL FIELD

The present invention relates to a water absorbing resin having a siloxane skeleton and a cosmetic containing the same.

BACKGROUND ART

Water-soluble or water-swellable polymer compounds such as acrylic polymers, guar gum and cellulose are used to increase the viscosity of an aqueous composition such as an aqueous solution and an oil-in-water (O/W) type emulsion.

An acrylic polymer with its carboxylic groups being neutralized thickens an aqueous solution and oil-in-water (O/W) type emulsion, but makes them sticky. An acrylic polymer having a long-chain alkyl group has thickening capability, together with capability of emulsifying silicone oils to form O/W type emulsions, but it gives sticky feeling. An acrylic polymer having tris(trimethylsiloxy) structure (Patent Literature 1) is insufficient in thickening capability. Guar gum and cellulose realize lower stickiness compared to the acrylic polymers, but further improvement is desirable since they have insufficient thickening capability.

CITATION LIST

Patent Literature

Patent LITERATURE 1: Japanese Unexamined Patent Application Publication (Kokai) No. 2006-282599

SUMMARY OF INVENTION

Technical Problem

The present invention was accomplished in view of the above-described circumstances. It is an object of the present invention to provide a water absorbing resin having a siloxane skeleton that is capable of thickening an aqueous composition while preventing stickiness, together with a cosmetic containing the same.

Solution to Problem

To solve the foregoing problems, the present invention provides a water absorbing resin having a siloxane skeleton, being a copolymer comprising: a structural unit derived from a polymerizable vinyl monomer (A) shown by the following general formula (1),

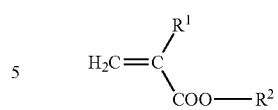

wherein, $R^1$ represents a hydrogen atom or a hydrocarbon group having 1 to 3 carbon atoms; $R^2$ represents a hydrocarbon group having 1 to 6 carbon atoms or a group shown by the following general formula (2); with the polymerizable vinyl monomer (A) optionally being a combination of the polymerizable vinyl monomers that differ in $R^2$;

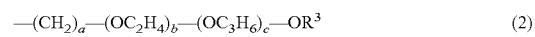

wherein, "a" is an integer of 1 to 4, $0 \le b \le 30$, $0 \le c \le 30$, and $0 \le b+c \le 40$; $R^3$ represents a hydrogen atom or a hydrocarbon group having 1 to 4 carbon atoms;

a structural unit derived from a polymerizable vinyl monomer (B) shown by the following general formula (3),

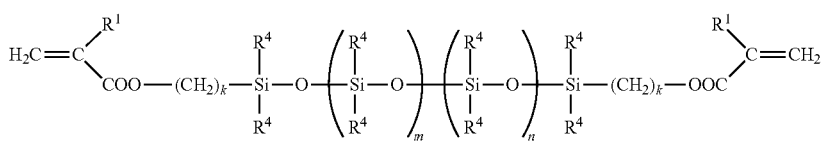

wherein, $R^1$ is as described above; X represents a hydrogen atom, an alkaline metal ion, an ammonium ion, or an organic ammonium ion; with the polymerizable vinyl monomer (B) optionally being a combination of the polymerizable vinyl monomers that differ in X;

a structural unit derived from an organopolysiloxane (C) having polymerizable groups at the both terminals thereof shown by the following general formula (4),

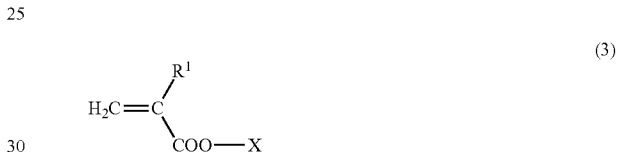

wherein, "k" is an integer of 1 to 4; $R^1$ is as described above; $R^4$ represents a hydrocarbon group having 1 to 8 carbon atoms; $R^5$ represents $R^4$ or a group shown by the general formula (2); and "m" and "n" are integers of $0 \le m \le 100$ and $0 \le n \le 20$ satisfying $0 \le m+n \le 100$.

The water absorbing resin having a siloxane skeleton like this is capable of thickening an aqueous composition without making them sticky.

The water absorbing resin having a siloxane skeleton is preferably a copolymer that contains 50 to 90% by mass of the structural unit derived from the polymerizable vinyl monomer (A), 10 to 50% by mass of the structural unit derived from the polymerizable vinyl monomer (B), and 2 to 30% by mass of the structural unit derived from the organopolysiloxane (C) in a ratio relative to the mass of the water absorbing resin.

The water absorbing resin that has the ratio of each structural unit like this securely effects thickening of water by being mixed thereto, and enables a cosmetic material using the same to provide more superior usability such as lightly spreading and smooth touch while preventing stickiness during the application.

Preferably, the water absorbing resin having a siloxane skeleton further comprises a structural unit derived from a polymerizable vinyl monomer (D) having an organopolysiloxane group shown by the following general formula (5),

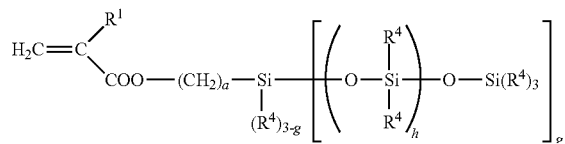

(5)

wherein, "a", $R^1$, and $R^4$ are as described above; "g" is an integer of 1 to 3, and "h" is an integer of 0 to 500 on average.

When the water absorbing resin having a siloxane skeleton contains the structural unit derived from the polymerizable vinyl monomer (D), it is possible to thicken an aqueous composition much higher, and to obtain lightly spreading and smooth touch while preventing stickiness during the application, in case of using the water absorbing resin as a cosmetic material.

In the water absorbing resin having a siloxane skeleton, X in the structural unit derived from the polymerizable vinyl monomer (B) is preferably a combination of a hydrogen atom and a sodium ion, wherein the sodium ion/the hydrogen atom ≥0.2 (molar ratio).

The water absorbing resin having such a siloxane skeleton is particularly preferable for use as a cosmetic material.

The present invention also provides a cosmetic comprising 0.1 to 10% by mass of the water absorbing resin having a siloxane skeleton described above.

The inventive cosmetic is capable of preventing stickiness during the application and giving excellent usability such as lightly spreading and smooth touch.

Preferably, the cosmetic further comprises an oil material (E) selected from the group consisting of silicone oils, hydrocarbon oils, ester oils, and glyceride oils.

Preferably, the cosmetic further comprises an alcohol (F) having 2 to 12 carbon atoms.

The cosmetic becomes more preferable when it contains an oil material (E) selected from silicone oils, hydrocarbon oils, ester oils, and glyceride oils; or an alcohol (F) having 2 to 12 carbon atoms in addition to the water absorbing resin having a siloxane skeleton of the present invention.

Preferably, the cosmetic further comprises a water-soluble or water-swellable polymer (G).

The cosmetic like this realizes sufficient film forming property with further preventing stickiness, and is more preferable as a cosmetic thereby.

Preferably, the cosmetic further comprises powder and/or colorant as a component (H).

The inventive cosmetic can contain the component (H) as described above in accordance with the dosage form and use of the cosmetic.

In this case, the component (H) preferably contains polyethylene powder, polypropylene powder, spherical powder of silicone elastomer, spherical polymethylsilsesquioxane powder, spherical powder of silicone elastomer coated with polymethylsilsesquioxane, or polyurethane powder.

The component (H) like this enables a cosmetic (product) to improve the stability with days and the touch, and is preferable thereby.

Preferably, the cosmetic further comprises a surfactant (I).

In this case, the surfactant is preferably selected from the group consisting of polyoxyalkylene-modified linear or branched organopolysiloxanes, polyglycerin-modified linear or branched organopolysiloxanes, and alkyl co-modified organopolysiloxanes thereof.

As described above, the cosmetic can contain a surfactant (I) in accordance with the object.

Preferably, the cosmetic further comprises a composition (J) composed of a liquid oil material and a crosslinked organopolysiloxane polymer other than the water absorbing resin having a siloxane skeleton.

The cosmetic comprising the composition (J) like this becomes excellent in stability.

Preferably, the cosmetic further comprises a composition (K) composed of a liquid oil material and a crosslinked organopolysiloxane polymer having a polyether group and/or a polyglycerin group other than the water absorbing resin having a siloxane skeleton.

In this case, the crosslinked organopolysiloxane polymer having a polyether group and/or a polyglycerin group is preferably a crosslinked organopolysiloxane polymer prepared from methylhydrogenpolysiloxane grafted with a polyoxyethylene chain and/or methylhydrogenpolysiloxane grafted with a polyglycerin chain.

The cosmetic comprising the component (K) like this is preferable since it improves the touch as a cosmetic.

Preferably, the cosmetic further comprises a silicone resin (L) selected from the group consisting of a silicone network compound containing an $SiO_2$ unit and/or an $RSiO_{3/2}$ unit (R represents an alkyl group), and a linear acryl/silicone graft- or block-copolymer.

In this case, the silicone network compound is preferably at least one resin selected from the group consisting of resins composed of an $R_3SiO_{1/2}$ unit and an $SiO_2$ unit; resins composed of an $R_3SiO_{1/2}$ unit, an $R_2SiO$ unit, and an $SiO_2$ unit; resins composed of an $R_3SiO_{1/2}$ unit and an $RSiO_{3/2}$ unit; resins composed of an $R_3SiO_{1/2}$ unit, an $R_2SiO$ unit, and an $RSiO_{3/2}$ unit; and resins composed of an $R_3SiO_{1/2}$ unit, an $R_2SiO$ unit, an $RSiO_{3/2}$ unit, and an $SiO_2$ unit.

The silicone network compound preferably contains at least one moiety selected from the group consisting of pyrrolidone moieties, long chain alkyl moieties, polyoxyalkylene moieties, fluoroalkyl moieties, and amino moieties.

The linear acryl/silicone graft- or block-copolymer preferably contains at least one organic group selected from the group consisting of pyrrolidone groups, long chain alkyl groups, polyoxyalkylene groups, fluoroalkyl groups, and anionic carboxy groups.

The cosmetic containing the silicone resin (L) like this is more preferable as a cosmetic since it has sufficient film forming property and is provided with gloss.

Preferably, the cosmetic further comprises an ultraviolet light protective component (M).

The ultraviolet light protective component (M) like this is usable and suitable as a material for a skincare cosmetic, a makeup cosmetic, an ultraviolet light protective cosmetic, etc.

The cosmetic is preferably an aqueous cosmetic selected from the group consisting of skincare cosmetics, hair cosmetics, antiperspirants, makeup cosmetics, and ultraviolet light protective cosmetics.

The inventive water absorbing resin having a siloxane skeleton is capable of thickening an aqueous composition without making it sticky, and is usable and suitable for a material of a skincare cosmetic, a hair cosmetic, an antiperspirant, a makeup cosmetic, and an ultraviolet light protective cosmetic in an aqueous system.

The cosmetic is preferably in a form selected from liquid, emulsion, cream, solid, paste, gel, and mousse.

The inventive water absorbing resin having a siloxane skeleton is particularly suitable for a material of cosmetic in a form described above.

The cosmetic is preferably an O/W-type cream, foundation, shampoo, or rinse.

The cosmetic like this can be remarkably thickened with the inventive water absorbing resin having a siloxane skeleton, and is preferable thereby.

Advantageous Effects of Invention

The inventive water absorbing resin having a siloxane skeleton is capable of thickening an aqueous composition without making it sticky. The inventive cosmetic is capable of preventing stickiness during the application and giving excellent usability such as lightly spreading and smooth touch.

DESCRIPTION OF EMBODIMENTS

The present inventors have diligently studied to solve such a problem. The present inventors have consequently found that the copolymer obtained from a plurality kinds of a particular polymerizable monomers (two or more kinds thereof) and an organopolysiloxane having polymerizable groups at the both terminals thereof is superior water absorbing resin; thereby completing the present invention.

That is, the present invention is a water absorbing resin having a siloxane skeleton which is a copolymer containing a structural unit derived from a polymerizable vinyl monomer (A) described below, a structural unit derived from a polymerizable vinyl monomer (B) described below, and a structural unit derived from an organopolysiloxane (C) described below.

Polymerizable Vinyl Monomer (A)

The polymerizable vinyl monomer (A) is a monomer shown by the following general formula (1),

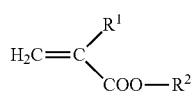

(1)

wherein, $R^1$ represents a hydrogen atom or a hydrocarbon group having 1 to 3 carbon atoms; $R^2$ represents a hydrocarbon group having 1 to 6 carbon atoms or a group shown by the following general formula (2), with the polymerizable vinyl monomer (A) optionally being a combination of the polymerizable vinyl monomers that differ in $R^2$;

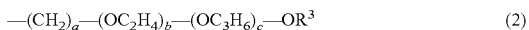

(2)

wherein, "a" is an integer of 1 to 4, $0 \leq b \leq 30$, $0 \leq c \leq 30$, and $0 \leq b+c \leq 40$; $R^3$ represents a hydrogen atom or a hydrocarbon group having 1 to 4 carbon atoms.

Illustrative examples of the hydrocarbon group having 1 to 3 carbon atoms of $R^1$ include a methyl group, an ethyl group, and a propyl group, preferably a methyl group. Illustrative examples of the hydrocarbon group having 1 to 6 carbon atoms of $R^2$ include a methyl group, an ethyl group, and an n-propyl group, an isopropyl group, an n-butyl group, and an n-hexyl group, preferably a methyl group.

As examples of the polymerizable vinyl monomer shown by the general formula (1) when $R^2$ is a hydrocarbon group having 1 to 6 carbon atoms, (meth)acrylate esters can be illustrated including methyl methacrylate, isopropyl methacrylate, n-butyl acrylate, and n-hexyl acrylate.

Illustrative examples of the (poly)oxyalkylene group of the general formula (2) of $R^2$ include types of polyoxyethylene, polyoxypropylene, block copolymers of polyethyleneoxide and polypropyleneoxide.

In the general formula (2), "a" is an integer of 1 to 4, preferably 2 or 3; "b" and "c" are numbers of $0 \leq b \leq 30$ and $0 \leq c \leq 30$ satisfying $0 \leq b+c \leq 40$, and are preferably $0 \leq b \leq 20$ and $0 \leq c \leq 20$.

As illustrative examples of polymerizable vinyl monomer shown by the general formula (1) when $R^2$ is the group shown by the general formula (2), ethylene glycol methyl ether acrylate, ethylene glycol n-butyl ether acrylate, diethylene glycol methyl ether methacrylate, triethylene glycol methyl ether acrylate, tetraethylene glycol methyl ether methacrylate, polyethylene glycol (polymerization degree: about 9) methyl ether methacrylate, dipropylene glycol methyl ether acrylate, etc. can be listed, and use of polyethylene glycol (polymerization degree: 2 to 10) methyl ether methacrylate is preferable. Illustrative examples of the trade name of the component (A) like this include BLEMMER PME-100, BLEMMER PME-200, BLEMMER PME-400, BLEMMER PP-1000, BLEMMER PP-500, and BLEMMER PP-800 (manufactured by NOF CORPORATION); NK eater M-20G, NK eater M-40G, and NK eater M-90G (manufactured by SHIN-NAKAMURA CHEMICAL CO LTD.); and CBA Viscoat 190 (manufactured by OSAKA ORGANIC CHEMICAL INDUSTRY LTD.).

Polymerizable Vinyl Monomer (B)

The polymerizable vinyl monomer (B) is a monomer shown by the following general formula (3),

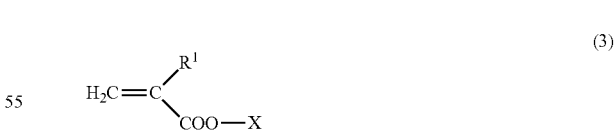

(3)

wherein, $R^1$ is as described above; X represents a hydrogen atom, an alkaline metal ion, an ammonium ion, or an organic ammonium ion, with the polymerizable vinyl monomer (B) optionally being a combination of the polymerizable vinyl monomers that differ in X.

Illustrative examples of X include a hydrogen atom, a sodium ion, a potassium ion, an ammonium ion, and an alkanol ammonium ion, and a sodium ion is particularly preferable.

The component (B) in which X is not a hydrogen atom can be obtained by neutralizing the component (B) in which X is a hydrogen atom with a basic material. Illustrative examples of the basic material include hydroxides of alkaline metals such as sodium hydroxide, potassium hydroxide, and lithium hydroxide; and ammonium such as ammonium, primary alkylammonium, secondary alkylammonium, and tertiary alkylammonium. Among them, sodium hydroxide is most common and is preferable. The neutralization reaction is preferably performed at a temperature of 10 to 80° C., more preferably 20 to 50° C. The neutralization reaction to form a salt can be performed before radical polymerization or after radical polymerization, or by neutralization separated to multi stages.

In the structural unit derived from the polymerizable vinyl monomer (B) in the inventive water absorbing resin having a siloxane skeleton, X is preferably a combination of a hydrogen atom and a sodium ion, and the sodium ion/the hydrogen atom ≥0.2 (molar ratio). That is, the degree of neutralization of the inventive water absorbing resin, which is based on the molar number of acid radical (—COOH) in the water absorbing resin and is a molar ratio of the molar number of base (—COOX)/the molar number of acid radical (—COOH), is preferably 0.2 or more, 1.0 to 0.2 and further 1.0 to 0.4 in particular, and is more preferably 0.8 to 0.5.

Organopolysiloxane (C)

The organopolysiloxane (C) is an organopolysiloxane having polymerizable groups at the both terminals thereof shown by the following general formula (4),

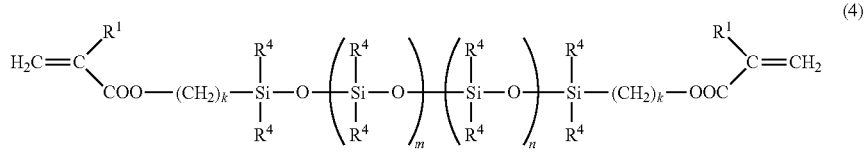

(4)

wherein, "k" is an integer of 1 to 4; $R^1$ is as described above; $R^4$ represents a hydrocarbon group having 1 to 8 carbon atoms; and $R^5$ represents $R^4$ or a group shown by the general formula (2); with the formula (4) including integers of $0 \le m \le 100$ and $0 \le n \le 20$ satisfying $0 \le m+n \le 100$.

Illustrative examples of $R^4$ include alkyl groups such as a methyl group, an ethyl group, and a butyl group; cycloalkyl groups such as a cyclopentyl group and a cyclohexyl group; aryl groups such as a phenyl group and a tolyl group; and aralkyl groups such as a benzyl group and a phenethyl group; preferably an alkyl group having 1 to 4 carbon atoms or a phenyl group, more preferably a methyl group.

Illustrative examples of the (poly)oxyalkylene group of the general formula (2) of $R^5$ include types of polyoxyethylene, polyoxypropylene, block copolymers of polyethyleneoxide and polypropyleneoxide.

In the general formula (4), "m" and "n" are integers of $0 \le m \le 100$ and $0 \le n \le 20$ satisfying $0 \le m+n \le 100$, and are preferably integers of $60 \le m \le 95$ and $0 \le n \le 10$.

The inventive water absorbing resin, having a siloxane skeleton of a copolymer that contains the structural unit derived from the polymerizable vinyl monomer (A), the structural unit derived from the polymerizable vinyl monomer (B), and the structural unit derived from the organopolysiloxane (C), is capable of thickening an aqueous composition without making it sticky.

The inventive water absorbing resin having a siloxane skeleton preferably contains 50 to 90% by mass of the structural unit derived from the polymerizable vinyl monomer (A), 10 to 50% by mass of the structural unit derived from the polymerizable vinyl monomer (B), and 2 to 30% by mass of the structural unit derived from the organopolysiloxane (C) in a ratio relative to the mass of the water absorbing resin.

The water absorbing resin that has such a ratio of each structural unit is preferable since it securely effects thickening of water by being mixed thereto, and enables a cosmetic material using the same to provide more superior usability such as lightly spreading and smooth touch while preventing stickiness during the application.

Preferably, the water absorbing resin having a siloxane skeleton further contains a structural unit derived from the following polymerizable vinyl monomer (D) having an organopolysiloxane group:

The polymerizable vinyl monomer (D) having an organopolysiloxane group shown by the following general formula (5),

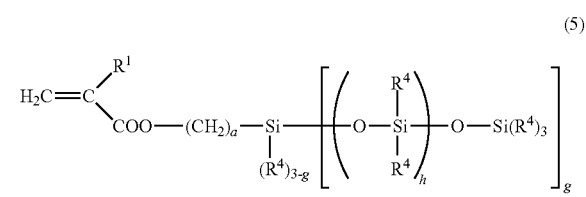

(5)

wherein, "a", $R^1$, and $R^4$ are as described above; "g" is an integer of 1 to 3, and "h" is an integer of 0 to 500 on average.

Illustrative examples of $R^4$ in the formula (5) include alkyl groups such as a methyl group, an ethyl group, and a butyl group; cycloalkyl groups such as a cyclopentyl group and a cyclohexyl group; aryl groups such as a phenyl group and a tolyl group; and aralkyl groups such as a benzyl group and a phenethyl group; preferably an alkyl group having 1 to 4 carbon atoms or a phenyl group, more preferably a methyl group.

Wherein, "h" is an integer with the average being 0 to 500, preferably 0 to 300, more preferably 0 to 250. The copolymer with "h" being 500 or less is preferable since it can be prepared without difficulty; "g" is an integer of 1 to 3; and particularly preferably, "g" is 1 and "h" is an integer of 10 to 250 on average.

The ratio of the structural unit derived from the polymerizable vinyl monomer (D) having an organopolysiloxane group is preferably 5 to 30% by mass, more preferably 5 to 20% by mass relative to the mass of the water absorbing resin having a siloxane skeleton. When the water absorbing resin having a siloxane skeleton contains the structural unit derived from the polymerizable vinyl monomer (D), it is possible to thicken an aqueous composition still more, and to give a cosmetic material that provides lightly spreading and smooth touch while preventing stickiness during the application.

The inventive water absorbing resin having a siloxane skeleton can be produced by common radical polymerization reactions. The polymerization is not particularly limited, but is usually performed such that the monomers of (A), (B), (C), and (D) in accordance with needs are diluted in solvent, and is polymerized with a radical initiator.

Illustrative examples of the solvent for the polymerization include water, ethanol, isopropanol, acetone, and toluene, preferably isopropanol.

The method for the radical polymerization, although it is not particularly limited, can be bulk polymerization, precipitation polymerization, reversed phase suspension polymerization, spray polymerization, dropwise polymerization, and solution polymerization. In view of the properties and easiness for controlling the polymerization, reversed phase suspension polymerization, spray polymerization, dropwise polymerization, and aqueous solution polymerization are preferable.

In performing the polymerization, dispersant can be used. Illustrative examples of the dispersant include cationic and amphoteric surfactants such as a sorbitan fatty acid ester and carboxymethyldimethylcetyl ammonium; anionic surfactants such as a sodium salt of polyoxyethylene dodecyl ether sulfate ester; and polymer dispersants such as cellulose ester, maleic-modified polybutadiene, and isopropyl methacrylate-quarternary salt of dimethylaminoethyl methacrylate. It is possible to use one or more kinds of these dispersants. The amount of the dispersant is preferably 0.01 to 5 parts by mass relative to 100 parts by mass of the monomers. The use of an ionic surfactant is preferable as the dispersant of the monomers particularly when reversed phase suspension polymerization is performed in view of preventing aggregation of particles of the highly water absorbing resin.

The polymerization initiator usable for synthesizing the inventive water absorbing resin having a siloxane skeleton is appropriately selected in accordance with the form of polymerization. Illustrative examples of the polymerization initiator like this include photolytic polymerization initiators, pyrolytic polymerization initiators, and redox polymerization initiators. The polymerization initiator is used in an amount of 0.001 to 10% by mole, preferably 0.001 to 5% by mole relative to the monomers. These amounts are preferable since the risk of causing coloring or stench is prevented when the polymerization initiator is used in an amount of 10% by mole or less, and the risk of increasing residual monomer is prevented when the amount is 0.001% by mole or more.

Illustrative examples of the photolytic polymerization initiator include benzoin derivatives, benzyl derivatives, acetophenone derivatives, benzophenone derivatives, and azo compounds. Illustrative examples of the pyrolytic polymerization initiator include persulfuric salts (sodium persulfate, potassium persulfate, ammonium persulfuric salts, etc.), peroxides (hydrogen peroxide, t-butyl peroxide, methyl ethyl ketone peroxide, etc.), azo compounds (dimethyl 2,2'-azobis(isobutyrate), 2,2'-azobis(2-amidinopropane) dihydrochloride, 2,2'-azobis[2-(2-imidazoline-2-yl)propane] dihydrochloride, etc.), and perchlorates (potassium perchlorate, sodium perchlorate, etc.).

Illustrative examples of the redox polymerization initiator include systems in which persulfuric salt or peroxide described above is combined with a reductive compound such as a sulfite, L-ascorbic acid, and a ferrous salt. It is also possible to combine a photolytic polymerization initiator and a pyrolytic polymerization initiator. Among them, peracid salts are preferable to attain the object of the present invention.

The polymerization initiator may be introduced at once or may be dissolved in solvent and introduced dropwisely. It is also possible to add the polymerization initiator in the course of the reaction as needed.

A desired water absorbing resin can be obtained by subjecting the water absorbing resin in a form of water-containing gel obtained by the polymerization to post treatments in accordance with needs such as cleaning and drying in order to remove the residual monomer or the residual initiator after the polymerization.

In case of cleaning, the solvent is not particularly limited, but illustrative examples thereof include water, acetone, alcohols, isoparaffins, and volatile silicones. The cleaning may be performed by using the solvent singly, or may be performed by combining or step-by-step using of the solvents.

The drying step is preferably performed by a drying method such as heat drying, hot-air drying, vacuum drying, infrared drying, micro-wave drying, freeze drying, dehydration by azeotroping with a hydrophobic organic solvent, or drying in high humidity using high temperature steam, although the drying process is not particularly limited unless it departs from conventional methods, and hot-air drying is more preferable. The drying temperature and time are not particularly limited, but the temperature of less than 150° C. and the drying time of less than 5 hours are preferable since this prevents problems of changing the property of resin, lowering of the water absorption ratio, and coloring.

The drying step can be followed by adjusting of the particle size in accordance with needs, or surface crosslinking to uniform the particle sizes. The particle size can be appropriately adjusted by polymerization, grinding, classification, granulation, and retrieving finely divided powders.

As a surface crosslinking agent used for the surface crosslinking, although various organic and inorganic crosslinking agents are usable, organic surface crosslinking agents are preferable. Illustrative examples thereof include polyhydric alcohols, epoxy compounds, polyvalent amines or condensates thereof with a haloepoxy compound, oxazoline compounds, and crosslinking agents capable of dehydration ester reaction formed from (mono-, di-, or poly-) oxazolidinone compound.

The inventive water absorbing resin having a siloxane skeleton can have any shape such as a sphere, a lump, a scale, a plate, an ovoid, a fibrous shape, granular shape in which particles are packed.

In the water absorbing resin having a siloxane skeleton described in the present application, the average particle size is not particularly limited, but the average particle size is preferably 100 nm or more and 1 mm or less, more preferably 300 nm or more and 500 µm or less when water is not absorbed thereinto (the heating loss after 150° C./3 hours is 5% or less). Incidentally, the average particle size is measured by the method, which is appropriately selected in accordance with the shape from a microscopic method, a light scattering method, a laser diffraction method, a liquid sedimentation method, an electric resistance method, etc.

The inventive water absorbing resin having a siloxane skeleton has crosslinking moieties and has a function of causing gelation of aqueous solvent to show thickening effect on aqueous compositions. The gelation described herein is a state in which low-viscosity liquid shows little or no fluidity by the water absorbing resin having a siloxane skeleton. The aqueous solvent may be water alone or a mixture of water and another organic solvent(s). The organic solvent to be mixed with is not particularly limited, but is preferably an amphipathic solvent(s). Illustrative examples of the amphipathic solvent include alcohols such as methanol, ethanol, propanol, and 2-propanol; ketones such as acetone; and ethers such as tetrahydrofuran and dioxane.

Antioxidants has a function to prevent oxidative degradation of polyether. The inventive water absorbing resin having a siloxane skeleton is prevented from lowering of the swell characteristics with time by adding the antioxidant. Illustrative examples of such an antioxidant include phenols, amine types, sulfur types, phosphorus types, waxes, and metal complexes thereof, as well as compounds derived from natural products such as vitamin C (L-ascorbic acid), vitamin E (α-tocopherol), and kojic acid as well as derivatives thereof. Most of them are commercially available and commercial antioxidants may be used usually.

The inventive cosmetic contains the water absorbing resin having a siloxane skeleton in an amount of 0.1 to 10% by mass, preferably 0.5 to 5.0% by mass in terms of solid content, that is the copolymer containing water that cannot be removed by an ordinal method, although the amount differs owing to a desired dosage form of the cosmetic. When the content of the water absorbing resin having a siloxane skeleton (copolymer) is in the above range, lightly spreading and smooth touch can be securely obtained while preventing stickiness during the application.

The inventive water absorbing resin having a siloxane skeleton is suitable as a thickening agent for a cosmetic material that contains water. In a cosmetic material containing a silicone oil material, the inventive water absorbing resin having a siloxane skeleton is also capable of functioning as an emulsifying agent for the silicone oil material to give an emulsion with fine texture. The inventive water absorbing resin is particularly suitable for forming an oil-in-water type emulsion, and is capable of giving a cosmetic with refreshing feel without greasy touch. The cosmetic containing the inventive water absorbing resin having a siloxane skeleton does not leave stickiness after volatilizing water. When an oil-in-water type emulsion is formed, the inventive water absorbing resin having a siloxane skeleton is preferably served as a 10 to 50% by mass of an oil-in-water type emulsion, and is appropriately diluted by adding water in case of use. The aqueous composition containing the inventive water absorbing resin having a siloxane skeleton may be blended to a cosmetic as a thickening agent or an emulsifying agent in a powdery state from which water of the aqueous composition has been removed.

The cosmetic according to the present invention includes aqueous, that is water-containing external cosmetics externally used for skin or hair such as skincare cosmetics, hair cosmetics, antiperspirants, makeup cosmetics, and ultraviolet light protective cosmetics.

Illustrative examples of the skincare cosmetic include milky lotion, cream, lotion, calamine lotion, cleansing, pack, oil liquid, massage cream, essence, a cleaner, deodorant, hand cream, lip cream, after shave lotion, and pre-shave lotion. Illustrative examples of the hair cosmetics include shampoo, rinse, conditioner, treatment, hair color, hair tonic, and setting agent. Illustrative examples of the ultraviolet light protective cosmetic include sun screen agent and sun tan agents. Other examples include makeup cosmetics such as make up base, liquid foundation, eye shadow, mascara, eye liner, eyebrow, and lipstick.

Illustrative examples of the inventive cosmetic preferably include an O/W-type cream, foundation, shampoo, or rinse in particular.

The inventive cosmetic can be in a form of liquid, emulsion, cream, solid, paste, gel, and mousse.

The inventive cosmetic can contain each of various components used for cosmetics such as an oil material (E) selected from the group consisting of silicone oils, hydrocarbon oils, ester oils, and glyceride oils; and an alcohol (F) having 2 to 12 carbon atoms in addition to the copolymer described above. Hereinafter, each component will be described.

As the oil material (E) selected from the group consisting of silicone oils, hydrocarbon oils, ester oils, and glyceride oils, any oil that is commonly used for cosmetics is usable whatever it is solid, semisolid, or liquid at ordinary temperature. Preferable examples thereof include silicon oils, hydrocarbon oils, ester oils, and glyceride oils in which a part of or all of the oil material is liquid at ordinary temperature. The inventive water absorbing resin having a siloxane skeleton excels in emulsifying silicon oils. Accordingly, the inventive cosmetic is particularly preferable when it contains a silicone oil.

Illustrative examples of the silicone oil include organopolysiloxanes that is liquid at ordinary temperature having a viscosity of 0.65 to 1000000 mm$^2$/s such as dimethylpolysiloxane, methylphenylpolysiloxane, methylhydrogenpolysiloxane, and dimethylsiloxane-methylphenylsiloxane copolymer; cyclosiloxanes such as octamethylcyclotetrasiloxane (D4), decamethylcyclopentasiloxane (D5), dodecamethylcyclohexasiloxane (D6), tetramethyltetrahydrogencyclotetrasiloxane (H4), and tetramethyltetraphenylcyclotetrasiloxane; branched siloxanes such as tristrimethylsiloxysilane (M3T), tetrakistrimethylsiloxysilane (M4Q), tristrimethylsiloxypropylsilane, tristrimethylsiloxylbutylsilane, tristrimethylsiloxyhexylsilane, and tristrimethylsiloxyphenylsilane; higher alkoxy-modified silicones such as stearoxysilicone, alkyl-modified silicones, amino-modified silicones, and fluorine-modified silicones. Preferable examples are dimethylpolysiloxane having a viscosity of 1 to 500000 mm$^2$/s, decamethylcyclopentasiloxane, dodecamethylcyclohexasiloxane, tristrimethylsiloxysilane, tetrakistrimethylsiloxysilane, and methylphenylpolysiloxane. The dimethylpolysiloxane having a viscosity of 1 to 500000 mm$^2$/s may be a solution composed of a low-viscosity silicone oil and a gummy dimethylpolysiloxane.

Illustrative examples of the hydrocarbon oils include ozokerite, α-olefin oligomer, volatile isoparaffin, volatile liquid isoparaffin, squalane, synthesized squalane, vegetable squalane, squalene, ceresin, paraffin, paraffin wax, liquid paraffin, liquid isoparaffin, pristane, polyisobutylene, microcrystalline wax, and Vaseline; illustrative examples of the higher fatty acid include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Illustrative examples of the ester oils include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate.

Illustrative examples of the glyceride oil include acetoglyceryl, glyceryl triisooctanoate, glyceryl triisostearate, glyceryl triisopalmitate, glyceryl monostearate, glyceryl di-2-heptylundecanoate, glyceryl trimyristate, and diglyceryl myristyl isostearate.

The inventive cosmetic may contain an oil material (hereinafter, other oil material) other than the oil material (E) selected from the group consisting of silicone oils, hydrocarbon oils, ester oils, and glyceride oils, and any oil that is commonly used for cosmetics is usable whatever it is solid, semisolid, or liquid at ordinary temperature. Preferable examples thereof include natural animal or vegetable oils, semisynthetic oils, higher fatty acids, higher alcohols having 11 or more carbon atoms, and fluorine-containing oils in which a part of or all of the oil material is liquid at room temperature.

Illustrative examples of the natural animal or vegetable oil and semisynthetic oil include avocado oil, linseed oil, almond oil, Ibota wax, perilla oil, olive oil, cacao butter, kapok wax, kaya oil, carnauba wax, liver oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, macadamia nut oil, beeswax, mink oil, cottonseed oil, cotton wax, Japan wax, Japan wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolin fatty acid, POE lanolin alcohol ether, POE lanolin alcohol acetate, polyethylene glycol lanolin fatty acid, POE hydrogenated lanolin alcohol ether, and egg yolk oil, wherein POE means polyoxyethylene.

Illustrative examples of the higher alcohol include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

Illustrative examples of the fluorine-containing oil include perfluoropolyether, perfluorodecalin, perfluorooctane, pitch fluoride, and fluoroalcohol. It is possible to use one kind or two or more kinds thereof in accordance with needs.

The cosmetic preferably contains the oil material (E) and the other oil material described above in an amount of 1.0 to 80.0% by mass, particularly preferably 1.0 to 50.0% by mass relative to the total mass of the cosmetic, although the amount is appropriately adjusted owing to the dosage form of the cosmetic. When the amount is 1.0% by mass or more, the oil material (E) is capable of exhibiting the effect thereof. When the amount is 80.0% by mass or less, the cosmetic becomes more preferable, in which stickiness is further prevented.

The inventive cosmetic may further contain an alcohol (F) having 2 to 12 carbon atoms. The component (F) is preferably a water-soluble mono- or poly-hydric alcohol. The compounding amount of the component (F) is preferably 0.1 to 50.0% by mass relative to the total mass of the cosmetic, although the amount is appropriately adjusted owing to a desired dosage form of the cosmetic. When the amount is 0.1% by mass or more, moisture retention, antifungal properties, or antibacterial properties are sufficiently provided. When the amount is 50.0% by mass or less, the cosmetic becomes more preferable, in which stickiness is further prevented.

Illustrative examples of the component (F) include lower monohydric alcohols such as ethanol, propanol, and isopropanol; polyhydric alcohols such as ethylene glycol, propylene glycol, 1,3-butylene glycol, diethylene glycol, dipropylene glycol, polyethylene glycol, isoprenol, glycerin, diglycerin, and triglycerin; sugar alcohols such as sorbitol and maltose.

The inventive cosmetic may contain one kind, or two or more kinds of water-soluble or water-swellable polymer (G). Illustrative examples thereof include vegetable polymers such as Arabic gum, tragacanth gum, arabinogalactan, locust bean gum (carob gum), guar gum, karaya gum, carrageenan, pectin, agar, quince seed (marmelo), starch (from rice, corn, potato, wheat), algae colloid, trant gum, and locust bean gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether and carboxyvinyl polymer; polyoxyethylene polymers; polyoxyethylene/polyoxypropylene copolymers; acrylic polymers such as sodium polyacrylate, polyethyl acrylate, and polyacrylamide; polyethyleneimine and cationic polymers; and inorganic water-soluble polymers such as bentonite, aluminum magnesium silicate, laponite, hectorite, and silicic anhydride. This component (G) can include a film-forming ingredient such as polyvinylalcohols and polyvinylpyrrolidone.

The compounding amount of the component (G) is preferably 0.01 to 25.0% by mass relative to the total amount of the cosmetic. When the amount is 0.01% by mass or more, film-forming thereof becomes sufficient. When the amount is 25.0% by mass or less, the cosmetic becomes more preferable, in which stickiness is further prevented.

The inventive cosmetic can contain a component(s) described below that has been used for cosmetics in accordance with needs, for example, powder and/or colorant (H), a surfactant (I), crosslinked organopolysiloxane (J, K), a silicone resin (L), and an ultraviolet light protective component (M).

Any powder and/or colorant that is used for common cosmetics can be used as the component (H) regardless of the shape (spherical, rod-like, acicular, plate-like, an indeterminate form, scale-like, spindle forms, etc.), the particle size (fumed, fine particle, pigment class, etc.), and the structure of particles (porous, non-porous). Illustrative examples thereof include inorganic powders, organic powders, powders of metal salt of surfactant, colored pigments, pearl pigments, metallic powder pigments, tar pigments and natural pigments as a color.

Illustrative examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectolitre, zeolite, ceramics powder, calcium secondary phosphate, alumina, aluminum hydroxide, boron nitride, boron nitride, and silica.

Illustrative examples of the organic powder include polyamide powder, polyester powder, polyethylene powder, polypropylene powder, polystyrene powder, polyurethane powder, benzoguanamine powder, polymethylbenzoguanamine powder, tetrafluoroethylene powder, polymethyl methacrylate powder, cellulose, silk powder, nylon powder, Nylon 12, Nylon 6, spherical silicone elastomer powder having a structure of crosslinked dimethylsilicone (see Japanese Unexamined Patent Application Publication No. H03-93834), spherical polymethylsilsesquioxane powder (see Japanese Unexamined Patent Application Publication No. H03-47848), spherical silicone elastomer powder coated with polymethyisilsesquioxane (see Japanese Unexamined Patent Application Publication No. H07-196815), styrene/acrylic acid copolymer, divinylbenzene/styrene copolymer, vinyl resin, urea resin, phenol resin, fluororesin, acrylic resin, melamine resin, epoxy resin, polycarbonate resin, powder of microcrystalline fiber, starch powder, and lauroyl lysine.

Illustrative examples of the powders of metal salt of surfactant (metal soap) include zinc stearate, aluminum stearate, calcium stearate, magnesium stearate, zinc myristate, magnesium myristate, zinc cetyl phosphate, calcium cetyl phosphate, and zinc sodium cetyl phosphate.

Illustrative examples of the colored pigment include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural pigments, and synthetic resin powder combining these powders.

Illustrative examples of the pearl pigment include titanium oxide-coated mica, titanium oxide-coated mica, bismuth oxychloride, titanium oxide-coated bismuth oxychioride, titanium oxide-coated talc, fish scales, and titanium oxide-coated colored mica. Illustrative examples of the metallic powder pigment include aluminum powder, copper powder, and stainless steel powder.

Illustrative examples of the tar pigment include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Illustrative examples of the natural pigment include carminic acid, laccaic acid, carthamin, brazilin, and crocin.

These powders may also be used after forming composite powder or being treated with a common oil material, silicone oil, a fluorine compound, or a surfactant. For example, the powder may or may not be subjected to surface treatment beforehand such as fluorine compound treatment, silicone resin treatment, pendant treatment, silane coupling agent treatment, titanate coupling agent treatment, oil material treatment, N-acyl lysine treatment, polyacrylic acid treatment, metal soap treatment, amino acid treatment, inorganic compound treatment, plasma treatment, or mechanochemical treatment. It is possible to use one kind, or two or more kinds thereof.

Preferably, spherical silicone elastomer powder, polyethylene powder, polypropylene powder, polytetrafluoroethylene powder, spherical polymethylsilsesquioxane powder, spherical silicone elastomer powder coated with polymethylsilsesquioxane, and polyurethane powder are used since they enable a product to improve the stability with days and the touch.

The compounding amount of the powder and/or colorant (H) is generally 0.1 to 50% by mass, preferably 0.5 to 30% by mass relative to the total mass of the cosmetic, although the amount largely varies owing to a desired dosage form of the cosmetic.

The surfactant (I) include nonionic, anionic, cationic, and amphoteric surfactants, and is selected in accordance with a desired cosmetic. For example, a nonionic surfactant is preferably used for skin cream, an anionic surfactant or betaine (amphoteric) surfactant is preferably used for shampoo, and cationic surfactant is preferably used for rinse.

Illustrative examples of the nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxane (see Japanese Patent No. 2137062, Japanese Unexamined Patent Application Publication No. H07-330907), polyglycerin-modified organopolysiloxane (see Examined Japanese Patent Application Publication No. S62-34039, Japanese Patent No. 2613124, Japanese Patent No. 2844453, Japanese Unexamined Patent Application Publication No. 2002-179798), polyoxyalkylene/alkyl-comodified organopolysiloxane (see Japanese Unexamined Patent Application Publication No. S61-90732, Japanese Unexamined Patent Application Publication No. H09-59386), alkanolamide, sugar ethers, and sugar amides.

Preferably, polyoxyalkylene-modified linear or branched organopolysiloxane, polyglycerin-modified linear or branched organopolysiloxane, and alkyl-comodified organopolysiloxane thereof are used.

Illustrative examples of the anionic surfactant include fatty acid soaps such as sodium stearate and triethanolamine palmitate, alkylether carboxylic acids and salts thereof, carboxylate of condensates of amino acids with fatty acids, alkyl sulfonic acid, alkenesulfonic salts, sulfonic salts of fatty acid esters, sulfonic salts of fatty acid amide, sulfonic salts of alkylsulfonic salts and the formalin condensates thereof, salts of alkyl sulfate esters, salts of secondary higher alcohol sulfate esters, salts of alkyl/allyl ether sulfate esters, salts of sulfate ester of fatty acid ester, salts of sulfate ester of fatty acid alkylolamide, salts of sulfate ester such as Turkey Red oil, alkyl phosphoric salts, ether phosphoric salts, alkylallylether phosphoric salts, amide phosphoric salts, and N-acylamino surfactants.

Illustrative examples of the cationic surfactant include amine salts such as alkylamine salts, amine salts of polyamine and amino alcohol fatty acid derivatives, alkyl quaternary ammonium salts, aromatic quaternary ammonium salts, pyridinium salts, and imidazolium salts.

Illustrative examples of the amphoteric surfactant include betaine, aminocarboxylic salts, and imidazoline derivatives.

The compounding amount of the surfactant (I) is preferably 0.1 to 20% by mass, more preferably 0.5 to 10% by mass relative to the total mass of the cosmetic.

The inventive cosmetic may further contain a composition (J) composed of a liquid oil material and a crosslinked organopolysiloxane polymer other than the water absorbing resin having a siloxane skeleton. The crosslinked organopolysiloxane polymer can be obtained by reaction of alkylhydrogenpolysiloxane and a crosslinking agent that has reactive vinyl-type unsaturated groups at the terminals of the molecular chain. Illustrative examples of the alkylhydrogenpolysiloxane include linear or partially branched methylhydrogenpolysiloxane and methylhydrogenpolysiloxane grafted with an alkyl chain(s) having 6 to 20 carbon atoms. The molecule have to contain two or more hydrogen atoms bonded to silicon atoms on average. Examples of the crosslinking agent include the one having two or more vinyl-type reactive moieties in the molecule such as methylvinylpolysiloxane and α,ω-alkenyldiene. Illustrative examples thereof include compositions described in each publications of Japanese patent No. 1925781, Japanese patent No. 1932769, and WO 03-24413. The crosslinked methylpolysiloxane is swelled with a liquid oil material such as low-viscosity silicone with the viscosity of 0.65 to 100.0 mm$^2$/second (25° C.), hydrocarbon oil such as liquid paraffin, squalane, isododecane, glyceride oil such as trioctanoyne, and ester oils in an amount of the own weight or more, for example.

The compounding amount of the crosslinked organopolysiloxane (J) swelled with an oil material is preferably 0.5 to 60% by mass, more preferably 2 to 50% by mass, further preferably 3 to 40% by mass relative to the total mass of the cosmetic, although the amount depends on the type and amount of the oil material.

The inventive cosmetic may further contain a composition (K) composed of a liquid oil material and a crosslinked organopolysiloxane polymer having a polyether group and/or a polyglycerin group. The crosslinked organopolysiloxane polymer having a polyether group and/or a polyglycerin group can be obtained by reaction of alkylhydrogenpolysiloxane and a crosslinking agent that has reactive vinyl-type unsaturated groups at the terminals of the molecular chain. Illustrative examples of the alkylhydrogenpolysiloxane include methylhydrogenpolysiloxane grafted with a polyoxyethylene chain(s), and methylhydrogenpolysiloxane grafted with a polyglycerin chain(s). The molecule have to contain two or more hydrogen atoms bonded to silicon atoms on average. The crosslinked organopolysiloxane polymer is swelled with low-viscosity silicone having a viscosity of 0.65 to 100.0 mm$^2$/second (25° C.), hydrocarbon oil such as liquid paraffin, squalane, isododecane, glyceride oil such as trioctanoyne, and ester oils in an amount of the own weight or more.

Examples of the crosslinking agent include the one having two or more vinyl-type reactive moieties in the molecule such as methylvinylpolysiloxane, α,ω-alkenyldiene, glycerin triallyl ether, polyoxyalkynylated glycerin triallyl ether, trimethylolpropane triallyl ether, polyoxyalkynylated trimethyloipropane triallyl ether. The crosslinked reaction product of these has at least one hydrophilic group. Preferable composition (K) include compositions described in each publications of Japanese patent No. 2631772, Japanese Unexamined Patent Application Publication No. H09-136813, Japanese Unexamined Patent Application Publication No. 2001-342255, and WO 03/20828.

The compounding amount of the crosslinked organopolysiloxane (K) swelled with an oil material is preferably 0.5 to 60% by mass, more preferably 2 to 50% by mass, further preferably 3 to 40% by mass relative to the total mass of the cosmetic, although the amount depends on the type and amount of the oil material.

The inventive cosmetic may further contain a silicone resin (L) selected from the group consisting of silicone network compounds containing an SiO$_2$ unit(s) and/or an RSiO$_{3/2}$ unit(s) (R represents an alkyl group), and a linear acryl/silicone graft- or block-copolymer. The silicone resin (L) is preferably gummy or solid at ordinary temperature. The silicone network compound may contain at least one moiety selected from the group consisting of pyrrolidone moieties, long chain alkyl moieties, polyoxyalkylene moieties, fluoroalkyl moieties, and amino moieties. The linear acryl/silicone graft- or block-copolymer may contain at least one organic group selected from the group consisting of pyrrolidone groups, long chain alkyl groups, polyoxyalkylene groups, fluoroalkyl groups, and anionic carboxy groups.

The silicone network compound is preferably a silicone network compound represented by MQ, MDQ, MT, MDT, or MDTQ (wherein M, D, T, and Q represent an R$_3$SiO$_{1/2}$ unit, an R$_2$SiO unit, an RSiO$_{3/2}$ unit, and an SiO$_2$ unit respectively).

That is, the silicone network compound is preferably at least one resin selected from the group consisting of resins composed of an R$_3$SiO$_{1/2}$ unit and an SiO$_2$ unit; resins composed of an R$_3$SiO$_{1/2}$ unit, an R$_2$SiO unit, and an SiO$_2$ unit; resins composed of an R$_3$SiO$_{1/2}$ unit and an RSiO$_{3/2}$ unit; resins composed of an R$_3$SiO$_{1/2}$ unit, an R$_2$SiO unit, and an RSiO$_{3/2}$ unit; and resins composed of an R$_3$SiO$_{1/2}$ unit, an R$_2$SiO unit, an RSiO$_{3/2}$ unit, and an SiO$_2$ unit.

The silicone resins such as the acryl silicone resins and the silicone network compounds can be dissolved in solvent such as low-viscosity silicone oil, volatile silicone oil, etc. In each case when this silicone resin (L) is used, the amount of the resin (L) is preferably 0.1 to 20% by mass, further preferably 1 to 10% by mass relative to the total mass of the cosmetic.

The inventive cosmetic may further contain an ultraviolet light protective component (M). Illustrative examples of the ultraviolet light protective component (M) include inorganic pigments and metal powders that are capable of scattering ultraviolet light among the ones described above, together with organic ultraviolet absorbing agents. When the inorganic ultraviolet scattering agent is blended, it is particularly preferable to incorporate it in the form of dispersion in an oil material. As an example thereof in which titanium oxide is used as the pigment that is capable of scattering ultraviolet light, and D5 is used as the oil material, SPD-T1, T2, T1S, T1V, T3V, and T5 (all of which are trade names of Shin-Etsu Chemical Co. Ltd.) are illustrated. As an example thereof in which zinc oxide is used as the pigment that is capable of scattering ultraviolet light, and D5 is used as the oil material, SPD-Z1, Z2, Z3, Z1S, Z3S, and Z5 (all of which are trade names of Shin-Etsu Chemical Co. Ltd.) are illustrated. As the oil material, M3T, M4Q, volatile hydrocarbon oil, or a non-volatile oil material can be used in placed of D5.

Illustrative examples of the organic ultraviolet light absorbents include benzoic acid base ultraviolet light absorbents such as p-aminobenzoic acid, ethyl p-aminobenzoate, glyceryl p-aminobenzoate, amyl p-dimethylaminobenzoate, octyl p-dimethylaminobenzoate, and ethyl 4-[N,N-di(2-hydroxypropyl)amino] benzoate; salicylic acid base ultraviolet light absorbents such as methyl salicylate, ethylene glycol salicylate, phenyl salicylate, octyl salicylate, benzyl salicylate, p-tert-butylphenyl salicylate, and homomentyl salicylate; cinnamic acid base ultraviolet light absorbents such as benzyl cinnamate, 2-ethoxyethyl p-methoxy cinnamate, octyl p-methoxy cinnamate, and glyceryl mono-2-ethylhexanoate di-p-methoxy cinnamate; urocanic acid base ultraviolet light absorbents such as urocanic acid and ethyl urocanate; benzophenone base ultraviolet light absorbents such as hydroxymethoxy benzophenone, hydroxymethoxy benzophenone sulfonic acid, sodium hydroxymethoxy benzophenone sulfonate, dihydroxymethoxy benzophenone, sodium dihydroxydimethoxy benzophenone disulfonate, 2,4-dihydroxy benzophenone, and tetrahydroxy benzophenone; dibenzoyl methane base ultraviolet light absorbents such as 4-tert-butyl-4'-methoxy-dibenzoyl methane; anthranilic acid base ultraviolet light absorbents such as mentyl anthranilate; benzotriazol derivatives such as 2-(2-hydroxy-5-methylphenyl)benzotriazol; and higher molecular weight derivatives thereof, and silane or siloxane derivatives thereof.

The compounding amount of the ultraviolet light protective component (M) is preferably 0.1 to 20% by mass, further preferably 1 to 10% by mass relative to the total mass of the cosmetic. Among the organic ultraviolet light absorbents described above, 2-ethylhexyl p-methoxy cinnamate, and 4-t-butyl-4'-methoxy-dibenzoylmethane are preferably used in particular.

The ultraviolet light protective component (M) can be the one in which an organic ultraviolet light absorbent is encapsulated in polymer powder. The polymer powder may or may not be hollow. The polymer powder preferably has an average primary particle size in a range of 0.1 to 50 μm, and may has a broad or sharp particle size distribution. Illustrative examples of the polymer include acryl resins, methacryl resins, styrene resins, urethane resins, polyethylene resins, polypropylene resins, polyethylene terephthalate resins, silicone resins, nylon resins, and acrylamide resins. Such polymer powder is preferably blended as powder in which an organic ultraviolet light protective agent is introduced thereto in a range of 0.1 to 30% by mass of the powder, and is particularly preferable to introduce 4-t-butyl-4'-methoxy dibenzoylmethane, which is a UV-A absorber.

The inventive cosmetic can contain other components that are commonly used in cosmetics such as oil-soluble gelling agents (including organic-modified clay minerals), resins, moisture retention agents, antiseptics, anti-microbial agents, perfumes, salts, antioxidants, pH adjustors, a chelating agents, refreshing agents, an anti-inflammatory agent, skin beautifying components (e.g., skin whitener, cell activator, rough dry skin improver, blood circulation promoter, skin astringent, and anti-seborrheic agent), vitamins, amino acids, nucleic acids, hormones, and clathrate compounds.

Illustrative examples of the oil-soluble gelling agent include metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate ester, dextrin stearate ester, and dextrin 2-ethylhexaminate palmitate ester; sucrose fatty acid esters such as sucrose palmitate ester and sucrose stearate ester; benzylidene derivatives of sorbitol such as monobenzylidene sorbitol and dibenzylidene sorbitol; and organic-modified clay minerals such as dimethylbenzyldodecyl ammonium montmorillonite clay and dimethyldioctadecyl ammonium montmorillonite clay. It is possible to use one kind, or two or more kinds thereof in accordance with needs.

Illustrative examples of the moisture retention agent include glycerin, sorbitol, propylene glycol, dipropylene glycol, 1,3-butylene glycol, glucose, xylitol, maltitol, polyethylene glycol, hyaluronic acid, chondroitin sulfuric acid, pyrrolidone carboxylic salts, polyoxyethylene methyl glycoside, and polyoxypropylene methylglycoside.

Illustrative examples of the antiseptic include alkyl p-oxybenzoate esters, benzoic acid, sodium benzoate, sorbic acid, potassium sorbate, and phenoxyethanol. Illustrative examples of the antibacterial agent include benzoic acid, salicylic acid, carbolic acid, sorbic acid, alkyl paraoxybenzoate esters, parachloromethacresol, hexachlorophene, benzalkonium chloride, chlorohexydine chloride, trichlorocarbanilide, triclosan, photosensitizers, and phenoxyethanol.

Illustrative examples of the antioxidant include tocopherol, butylhydroxyanisole, dibutylhydroxytoluene, phytic acid, and the antioxidants described above; illustrative examples of the pH adjustors include lactic acid, citric acid, glycolic acid, succinic acid, tartaric acid, dl-malic acid, potassium carbonate, sodium hydrogen carbonate, and ammonium hydrogen carbonate; illustrative examples of the chelating agents include alanine, sodium edetate, sodium polyphosphate, sodium metaphosphate, and phosphoric acid; illustrative examples of the refreshing agent include L-menthol and camphor; and illustrative examples of the anti-inflammatory agents include allantoin, glycyrrhetinic acid, glycyrrhizic acid, tranexamic acid, and azulene.

Illustrative examples of the skin-beautifying component include whitening agents such as placenta extract, arbutin, glutathione, and Yukinoshita extract; cell activators such as royal jelly, photosensitizers, cholesterol derivatives, and calf blood extract; rough and dry skin improvers; blood circulation improvers such as nonylic acid vanillyl amide, benzyl nicotinate, β-butoxyethyl nicotinate, capsaicin, zingerone, cantharis tincture, ichtammol, caffeine, tannic acid, α-borneol, tocopherol nicotinate, inositol hexanicotinate, cyclandelate, cinnarizine, tolazoline, acetyl choline, verapamil, cepharanthin, and γ-oryzanol; skin astringents such as zinc oxide and tannic acid; and anti-seborrheic agents such as sulfur and thianthol.

Illustrative examples of the vitamins include vitamin A such as vitamin A oil, retinol, retinyl acetate, and retinyl palmitate; vitamin B including vitamin B2 such as riboflavin, riboflavin butyrate, and flavin adenine nucleotide, vitamin B6 such as pyridoxine hydrochloride, pyridoxine dioctanoate, and pyridoxine tripalmitate, vitamin B12 and its derivatives, and vitamin B15 and its derivatives; vitamin C such as L-ascorbic acid, L-ascorbic acid dipalmitate ester, sodium (L-ascorbic acid)-2-sulfate, and dipotassium L-ascorbic acid phosphate diester; vitamin D such as ergocalciferol and cholecarciferol; vitamin E such as α-tocopherol, β-tocopherol, γ-tocopherol, dl-α-tocopheryl acetate, dl-α-tocopheryl nicotinate, and dl-α-tocopheryl succinate;

vitamin H; vitamin P; nicotinic acid derivatives such as nicotinic acid, benzyl nicotinate, and nicotinic acid amide; pantothenic acid derivatives such as calcium pantothenate, D-pantothenyl alcohol, pantothenyl ethyl ether, and acetyl-pantothenyl ethyl ether; and biotin.

Illustrative examples of the amino acids include glycine, valine, leucine, isoleucine, serine, threonine, phenylaranine, alginine, lysine, aspartic acid, glutamic acid, cystine, cysteine, methionine, and tryptophan; illustrative examples of the nucleic acid include deoxyribonucleic acid; and illustrative examples of the hormone include estradiol and ethenyl estradiol.

EXAMPLE

Hereinafter, the present invention will be described in more detail with reference to Synthesis Examples of the inventive water absorbing polymer and Examples of the inventive cosmetic, but the present invention is not limited thereto.

Synthesis Example 1

Into a 1 liter separable flask equipped with a stirring rod, 50 g of polyoxypropyl methacrylate (BLEMMER PP-1000, manufactured by NOF CORPORATION: having the following average structural formula (6)), 12 g of methacrylic acid, 6 g of silicone with the both terminal being methacryl-terminated and the side chain being modified with polyether shown by the following average structural formula (7), 100 g of isopropyl alcohol, and 0.034 g of dimethyl 2,2'-azobis (isobutyrate) (0.054% by mole relative to the total monomers) were introduced. This was stirred to be a homogeneous solution, and then heated to 80° C. while flowing nitrogen to be allowed to react for 8 hours. After cooling, this was partially neutralized by adding 11 g of 25% NaOH. Subsequently, the obtained gel was washed with excess isopropyl alcohol and was filtered to give powder. This was dried for 10 hours in a vacuum drier, and then grinded with a grinder to give target Water absorbing polymer particle 1 in a form of white powder (neutralization degree (a ratio of the methacrylic acid neutralized with alkali)=0.5 (molar ratio)).

6 g of silicone with the both terminal being methacryl-terminated and the side chain being modified with polyether shown by the above average structural formula (7), 100 g of isopropyl alcohol, and 0.034 g of dimethyl 2,2'-azobis (isobutyrate) (0.062% by mole relative to the total monomers) were introduced. This was stirred to be a homogeneous solution, and then heated to 80° C. while flowing nitrogen to be allowed to react for 8 hours. After cooling, this was partially neutralized by adding 11 g of 25% NaOH. Subsequently, the obtained gel was washed with excess isopropyl alcohol and was filtered to give powder. This was dried for 10 hours in a vacuum drier, and then grinded with a grinder to give target Water absorbing polymer particle 2 in a form of white powder (neutralization degree (a ratio of the methacrylic acid neutralized with alkali)=0.5 (molar ratio)).

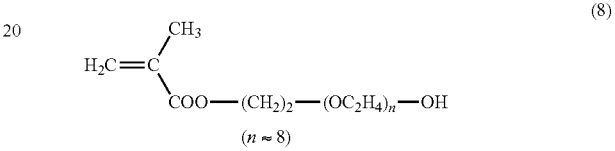

(8)

Synthesis Example 3

Into a 1 liter separable flask equipped with a stirring rod, 50 g of polyoxypropyl methacrylate (BLEMMER PP-1000, manufactured by NOF CORPORATION: having the above average structural formula (6)), 12 g of methacrylic acid, 6 g of silicone with the both terminal being methacryl-terminated and the side chain being modified with polyether shown by the following average structural formula (9), 100 g of isopropyl alcohol, and 0.034 g of dimethyl 2,2'-azobis (isobutyrate) (0.054% by mole relative to the total monomers) were introduced. This was stirred to be a homogeneous solution, and then heated to 80° C. while flowing nitrogen to be allowed to react for 8 hours. After cooling, this was partially neutralized by adding 11 g of 25% NaOH. Subsequently, the obtained gel was washed with excess

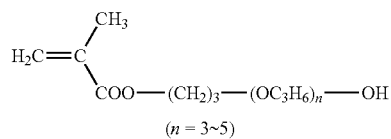

(6)

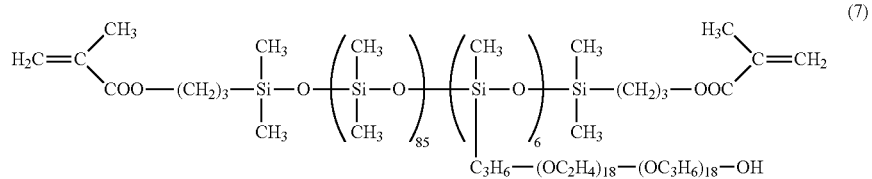

(7)

Synthesis Example 2

Into a 1 liter separable flask equipped with a stirring rod, 50 g of polyoxyethyl methacrylate (BLEMMER PME-400, manufactured by NOF CORPORATION: having the following average structural formula (8)), 12 g of methacrylic acid, isopropyl alcohol and was filtered to give powder. This was dried for 10 hours in a vacuum drier, and then grinded with a grinder to give target Water absorbing polymer particle 3 in a form of white powder (neutralization degree (a ratio of the methacrylic acid neutralized with alkali)=0.5 (molar ratio)).

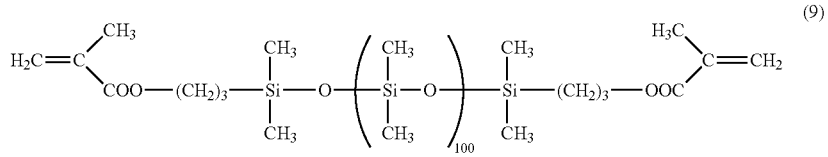

(9)

Synthesis Example 4

Into a 1 liter separable flask equipped with a stirring rod, 50 g of hexyl methacrylate, 12 g of methacrylic acid, 6 g of silicone with the both terminal being methacryl-terminated and the side chain being modified with polyether shown by the above average structural formula (7), 100 g of isopropyl alcohol, and 0.034 g of dimethyl 2,2'-azobis(isobutyrate) (0.034% by mole relative to the total monomers) were introduced. This was stirred to be a homogeneous solution, and then heated to 80° C. while flowing nitrogen to be allowed to react for 8 hours. After cooling, this was partially neutralized by adding 11 g of 25% NaOH. Subsequently, the obtained gel was washed with excess isopropyl alcohol and was filtered to give powder. This was dried for 10 hours in a vacuum drier, and then grinded with a grinder to give target Water absorbing polymer particle 4 in a form of white powder (neutralization degree (a ratio of the methacrylic acid neutralized with alkali)=0.5 (molar ratio)).

Synthesis Example 5

Into a 1 liter separable flask equipped with a stirring rod, 50 g of polyoxypropyl methacrylate (BLEMMER PP-1000, manufactured by NOF CORPORATION: having the above average structural formula (6)), 12 g of methacrylic acid, 6 g of silicone with the both terminal being methacryl-terminated and the side chain being modified with polyether shown by the above average structural formula (7), 8 g of singly methacryl-terminated silicone shown by the following average structural formula (10), 100 g of isopropyl alcohol, and 0.034 g of dimethyl 2,2'-azobis(isobutyrate) (0.054% by mole relative to the total monomers) were introduced. This was stirred to be a homogeneous solution, and then heated to 80° C. while flowing nitrogen to be allowed to react for 8 hours. After cooling, this was partially neutralized by adding 11 g of 25% NaOH. Subsequently, the obtained gel was washed with excess isopropyl alcohol and was filtered to give powder. This was dried for 10 hours in a vacuum drier, and then grinded with a grinder to give target Water absorbing polymer particle 5 in a form of white powder (neutralization degree (a ratio of the methacrylic acid neutralized with alkali)=0.5 (molar ratio)).

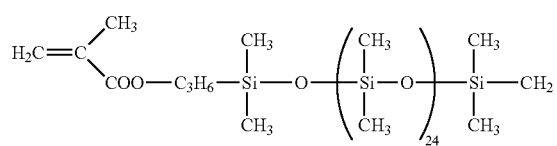

(10)

Synthesis Example 6

Into a 1 liter separable flask equipped with a stirring rod, 50 g of polyoxypropyl methacrylate (BLEMMER PP-1000, manufactured by NOF CORPORATION: having the above average structural formula (6)), 6 g of methacrylic acid, 6 g of sodium methacrylate, 6 g of silicone with the both terminal being methacryl-terminated and the side chain being modified with polyether shown by the above average structural formula (7), 100 g of isopropyl alcohol, and 0.034 g of dimethyl 2,2'-azobis(isobutyrate) (0.057% by mole relative to the total monomers) were introduced. This was heated to 80° C. while flowing nitrogen to be allowed to react for 8 hours. After cooling, the obtained gel was washed with excess isopropyl alcohol and was filtered to give powder. This was dried for 10 hours in a vacuum drier, and then grinded with a grinder to give target Water absorbing polymer particle 6 in a form of white powder (neutralization degree (a ratio of the methacrylic acid neutralized with alkali)=0.44 (molar ratio)).

Synthesis Example 7

Into a 1 liter separable flask equipped with a stirring rod, 20 g of polyoxypropyl methacrylate (BLEMMER PP-1000, manufactured by NOF CORPORATION: having the above average structural formula (6)), 10 g of polyoxyethyl methacrylate (BLEMMER PME-400, manufactured by NOF CORPORATION: having the above average structural formula (8)), 18 g of methacrylic acid, 6 g of silicone with the both terminal being methacryl-terminated and the side chain being modified with polyether shown by the above average structural formula (7), 100 g of isopropyl alcohol, and 0.027 g of dimethyl 2,2'-azobis(isobutyrate) (0.042% by mole relative to the total monomers) were introduced. This was heated to 80° C. while flowing nitrogen to be allowed to react for 8 hours. After cooling, this was partially neutralized by adding 11 g of 25% NaOH. Subsequently, the obtained gel was washed with excess isopropyl alcohol and was filtered to give powder. This was dried for 10 hours in a vacuum drier, and then grinded with a grinder to give target Water absorbing polymer particle 7 in a form of white powder (neutralization degree (a ratio of the methacrylic acid neutralized with alkali)=0.60 (molar ratio)).

Comparative Synthesis Example 1

Into a 1 liter separable flask equipped with a stirring rod, 50 g of polyoxypropyl methacrylate (BLEMMER PP-1000, manufactured by NOF CORPORATION: having the average structural formula (6)), 12 g of methacrylic acid, 2 g of polyethylene glycol dimethacrylate (BLEMMER PDE-600, manufactured by NOF CORPORATION: having the following average structural formula (11)), 100 g of isopropyl alcohol, and 0.034 g of dimethyl 2,2'-azobis(isobutyrate) (0.054% by mole relative to the total monomers) were introduced. This was stirred to be a homogeneous solution, and then heated to 80° C. while flowing nitrogen to be allowed to react for 8 hours. After cooling, this was partially neutralized by adding 11 g of 25% NaOH. Subsequently, the obtained gel was washed with excess isopropyl alcohol and was filtered to give powder. This was dried for 10 hours in a vacuum drier, and then grinded with a grinder to give target Water absorbing polymer particle 8 in a form of white powder (neutralization degree (a ratio of the methacrylic acid neutralized with alkali)=0.5 (molar ratio)).

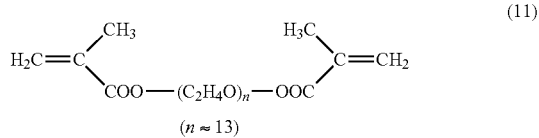

(11)

($n \approx 13$)

Examples 1 to 7, Comparative Example 1

Each white powder obtained from Synthesis Examples 1 to 7 and Comparative Synthesis Example 1 described above was mixed with water in a ratio of powder:water=5:95 (mass ratio), and was homogenized by using a spatula and the like. Then, this was mixed at a rotation rate of 3300 rpm for 15 minutes with High Shear Mixer manufactured by Silverson Machines, Inc. by using a high shear screen of a square hole type as the head, and was allowed to stand for 1 day in an atmosphere of 25° C. Then, this was subjected to measurement of viscosity and pH, and was checked for the situation of stickiness (Examples 1 to 7, Comparative Example 1). The results are shown in Table 1 described below.

TABLE 1

|  | Example 1 | Example 2 | Example 3 | Example 4 |
|---|---|---|---|---|
| Viscosity/mPa·s | 129000 | 87600 | 87400 | 72000 |
| pH | 6.7 | 6.7 | 6.8 | 6.4 |
| Stickiness | Good | Fair | Good | Good |

|  | Example 5 | Example 6 | Example 7 | Comparative Example 1 |
|---|---|---|---|---|
| Viscosity/mPa·s | 49600 | 69000 | 108000 | 63200 |
| pH | 7.0 | 6.8 | 6.7 | 6.4 |
| Stickiness | Fair | Good | Good | Bad |

The situation of stickiness was shown in the above Table 1 in accordance with following:
Good: scarcely sticky
Fair: slightly sticky
Bad: sticky The inventive water absorbing resin having a siloxane skeleton with water successfully effected thickening of water while preventing stickiness by being mixed to the water (Examples 1 to 7). On the other hand, the stickiness was increased in case of using a resin other than the water absorbing resin having a siloxane skeleton of the present invention (Comparative Example 1).

(Example 8) O/W-Type Cream

TABLE 2

|  | Components | % by mass |
|---|---|---|
| 1. | crosslinked dimethylpolysiloxane (*1) | 10.0 |
| 2. | isotridecyl isononanate | 5.0 |
| 3. | decamethylcyclopolysiloxane | 25.0 |
| 4. | polyether co-modified silicone (*2) | 0.5 |
| 5. | dipropylene glycol | 6.0 |

TABLE 2-continued

|  | Components | % by mass |
|---|---|---|
| 6. | glycerin | 5.0 |
| 7. | methyl cellulose (*3) | 5.0 |
| 8. | polyacrylamide-type emulsifier (*4) | 2.0 |
| 9. | antiseptic | Dosage |
| 10. | perfume | Dosage |
| 11. | Water absorbing polymer particle 1 | 5.0 |
| 12. | water | Residue |

(*1) KSG-15: manufactured by Shin-Etsu Chemical Co., Ltd.
(*2) KF-6011: manufactured by Shin-Etsu Chemical Co., Ltd.
(*3) METOLOSE SM-4000: manufactured by Shin-Etsu Chemical Co., Ltd.
(*4) SEPIGEL 305; manufactured by SEPIC (Production Method)
A: components 5 to 12 were mixed.
B: components 1 to 4 were mixed and dissolved, and added to the mixture obtained by A, which was stirred and emulsified.

The cream thus obtained was lightly spreadable and gave fresh and refreshing feel in use without stickiness and greasy touch.

(Example 9) O/W-Type Cream

TABLE 3

|  | Components | % by mass |
|---|---|---|
| 1. | crosslinked dimethylpolysiloxane (*1) | 10.0 |
| 2. | isotridecyl isononanate | 5.0 |
| 3. | decamethylcyclopolysiloxane | 25.0 |
| 4. | polyether co-modified silicone (*2) | 0.5 |
| 5. | dipropylene glycol | 6.0 |
| 6. | glycerin | 5.0 |
| 7. | methyl cellulose (*3) | 5.0 |
| 8. | polyacrylamide-type emulsifier (*4) | 2.0 |
| 9. | antiseptic | Dosage |
| 10. | perfume | Dosage |
| 11. | Water absorbing polymer particle 2 | 5.0 |
| 12. | water | Residue |

(*1) KSG-15: manufactured by Shin-Etsu Chemical Co., Ltd.
(*2) KF-6011: manufactured by Shin-Etsu Chemical Co., Ltd.
(*3) METOLOSE SM-4000: manufactured by Shin-Etsu Chemical Co., Ltd.
(*4) SEPIGEL 305; manufactured by SEPIC (Production Method)
A: components 5 to 12 were mixed.
B: components 1 to 4 were mixed and dissolved, and added to the mixture obtained by A, which was stirred and emulsified.

The cream thus obtained was lightly spreadable and gave fresh and refreshing feel in use without stickiness and greasy touch.

(Example 10) O/W-Type Cream

TABLE 4

|  | Components | % by mass |
|---|---|---|
| 1. | crosslinked dimethylpolysiloxane (*1) | 10.0 |
| 2. | isotridecyl isononanate | 5.0 |
| 3. | decamethylcyclopolysiloxane | 25.0 |
| 4. | polyether co-modified silicone (*2) | 0.5 |
| 5. | dipropylene glycol | 6.0 |
| 6. | glycerin | 5.0 |
| 7. | methyl cellulose (*3) | 5.0 |
| 8. | polyacrylamide-type emulsifier (*4) | 2.0 |
| 9. | antiseptic | Dosage |

TABLE 4-continued

| | Components | % by mass |
|---|---|---|
| 10. | perfume | Dosage |
| 11. | Water absorbing polymer particle 3 | 5.0 |
| 12. | water | Residue |

(*1) KSG-15: manufactured by Shin-Etsu Chemical Co., Ltd.
(*2) KF-6011: manufactured by Shin-Etsu Chemical Co., Ltd.
(*3) METOLOSE SM-4000: manufactured by Shin-Etsu Chemical Co., Ltd.
(*4) SEPIGEL 305; manufactured by SEPIC (Production Method)

A: components 5 to 12 were mixed.

B: components 1 to 4 were mixed and dissolved, and added to the mixture obtained by A, which was stirred and emulsified.

The cream thus obtained was lightly spreadable and gave fresh and refreshing feel in use without stickiness and greasy touch.

(Example 11) O/W-Type Cream

TABLE 5

| | Components | % by mass |
|---|---|---|
| 1. | crosslinked dimethylpolysiloxane (*1) | 10.0 |
| 2. | isotridecyl isononanate | 5.0 |
| 3. | decamethylcyclopolysiloxane | 25.0 |
| 4. | polyether co-modified silicone (*2) | 0.5 |
| 5. | dipropylene glycol | 6.0 |
| 6. | glycerin | 5.0 |
| 7. | methyl cellulose (*3) | 5.0 |
| 8. | polyacrylamide-type emulsifier (*4) | 2.0 |
| 9. | antiseptic | Dosage |
| 10. | perfume | Dosage |
| 11. | Water absorbing polymer particle 4 | 5.0 |
| 12. | water | Residue |

(*1) KSG-15: manufactured by Shin-Etsu Chemical Co., Ltd.
(*2) KF-6011: manufactured by Shin-Etsu Chemical Co., Ltd.
(*3) METOLOSE SM-4000: manufactured by Shin-Etsu Chemical Co., Ltd.
(*4) SEPIGEL 305; manufactured by SEPIC (Production Method)

A: components 5 to 12 were mixed.

B: components 1 to 4 were mixed and dissolved, and added to the mixture obtained by A, which was stirred and emulsified.

The cream thus obtained was lightly spreadable and gave fresh and refreshing feel in use without stickiness and greasy touch.

(Example 12) O/W-Type Cream

TABLE 6

| | Components | % by mass |
|---|---|---|
| 1. | crosslinked dimethylpolysiloxane (*1) | 10.0 |
| 2. | isotridecyl isononanate | 5.0 |
| 3. | decamethylcyclopolysiloxane | 25.0 |
| 4. | polyether co-modified silicone (*2) | 0.5 |
| 5. | dipropylene glycol | 6.0 |
| 6. | glycerin | 5.0 |
| 7. | methyl cellulose (*3) | 5.0 |
| 8. | polyacrylamide-type emulsifier (*4) | 2.0 |
| 9. | antiseptic | Dosage |

TABLE 6-continued

| | Components | % by mass |
|---|---|---|
| 10. | perfume | Dosage |
| 11. | Water absorbing polymer particle 5 | 5.0 |
| 12. | water | Residue |

(*1) KSG-15: manufactured by Shin-Etsu Chemical Co., Ltd.
(*2) KF-6011: manufactured by Shin-Etsu Chemical Co., Ltd.
(*3) METOLOSE SM-4000: manufactured by Shin-Etsu Chemical Co., Ltd.
(*4) SEPIGEL 305; manufactured by SEPIC (Production Method)

A: components 5 to 12 were mixed.

B: components 1 to 4 were mixed and dissolved, and added to the mixture obtained by A, which was stirred and emulsified.

The cream thus obtained was lightly spreadable and gave fresh and refreshing feel in use without stickiness and greasy touch.

(Example 13) O/W-Type Cream

TABLE 7

| | Components | % by mass |
|---|---|---|
| 1. | crosslinked dimethylpolysiloxane (*1) | 10.0 |
| 2. | isotridecyl isononanate | 5.0 |
| 3. | decamethylcyclopolysiloxane | 25.0 |
| 4. | polyether co-modified silicone (*2) | 0.5 |
| 5. | dipropylene glycol | 6.0 |
| 6. | glycerin | 5.0 |
| 7. | methyl cellulose (*3) | 5.0 |
| 8. | polyacrylamide-type emulsifier (*4) | 2.0 |
| 9. | antiseptic | Dosage |
| 10. | perfume | Dosage |
| 11. | Water absorbing polymer particle 6 | 5.0 |
| 12. | water | Residue |

(*1) KSG-15: manufactured by Shin-Etsu Chemical Co., Ltd.
(*2) KF-6011: manufactured by Shin-Etsu Chemical Co., Ltd.
(*3) METOLOSE SM-4000: manufactured by Shin-Etsu Chemical Co., Ltd.
(*4) SEPIGEL 305; manufactured by SEPIC (Production Method)

A: components 5 to 12 were mixed.

B: components 1 to 4 were mixed and dissolved, and added to the mixture obtained by A, which was stirred and emulsified.

The cream thus obtained was lightly spreadable and gave fresh and refreshing feel in use without stickiness and greasy touch.

(Comparative Example 2) O/W-Type Cream

TABLE 8

| | Components | % by mass |
|---|---|---|
| 1. | crosslinked dimethylpolysiloxane (*1) | 10.0 |
| 2. | isotridecyl isononanate | 5.0 |
| 3. | decamethylcyclopolysiloxane | 25.0 |
| 4. | polyether co-modified silicone (*2) | 0.5 |
| 5. | dipropylene glycol | 6.0 |
| 6. | glycerin | 5.0 |
| 7. | methyl cellulose (*3) | 5.0 |
| 8. | polyacrylamide-type emulsifier (*4) | 2.0 |
| 9. | antiseptic | Dosage |
| 10. | perfume | Dosage |

TABLE 8-continued

| | Components | % by mass |
|---|---|---|
| 11. | Water absorbing polymer particle 8 | 5.0 |
| 12. | water | Residue |

(*1) KSG-15: manufactured by Shin-Etsu Chemical Co., Ltd.
(*2) KF-6011: manufactured by Shin-Etsu Chemical Co., Ltd.
(*3) METOLOSE SM-4000: manufactured by Shin-Etsu Chemical Co., Ltd.
(*4) SEPIGEL 305; manufactured by SEPIC (Production Method)
A: components 5 to 12 were mixed.
B: components 1 to 4 were mixed and dissolved, and added to the mixture obtained by A, which was stirred and emulsified.

The cream thus obtained was dull in spreading and gave sticky touch in use.

(Example 14) O/W-Type UV-Cut Cream

TABLE 9

| | Components | % by mass |
|---|---|---|
| 1. | crosslinked dimethylpolysiloxane (*1) | 5.0 |
| 2. | cetyl isooctanate | 5.0 |
| 3. | octyl methoxycinnamate | 2.0 |
| 4. | titanium oxide/decamethyl-cyclopentasiloxane dispersion (*2) | 15.0 |
| 5. | polyether-modified silicone (*3) | 1.0 |
| 6. | polyether-modified silicone (*4) | 1.0 |
| 7. | acrylic amide-type mixture (*5) | 2.0 |
| 8. | propylene glycol | 5.0 |
| 9. | methyl cellulose (2% aqueous Solution) (*6) | 1.0 |
| 10. | antiseptic | Dosage |
| 11. | perfume | Dosage |
| 12. | Water absorbing polymer particle 7 | 5.0 |
| 13. | water | Residue |

(*1) KSG-15 (trade name): manufactured by Shin-Etsu Chemical Co., Ltd.
(*2) SPD-T5 (trade name): manufactured by Shin-Etsu Chemical Co., Ltd.
(*3) KF-6013 (trade name): manufactured by Shin-Etsu Chemical Co., Ltd.
(*4) KF-6011 (trade name): manufactured by Shin-Etsu Chemical Co., Ltd.
(*5) SEPIGEL 305 (trade name); manufactured by SEPIC
(*6) METOLOSE SM-4000 (trade name): manufactured by Shin-Etsu Chemical Co., Ltd.

(Production Method)
A: components 5 to 9, 10, 12, and 13 were mixed.
B: components 1 to 3 were mixed and heated, and added to the mixture obtained by A, which was stirred and emulsified.
C: component 4 was added to the emulsion obtained by B, which was stirred and emulsified. Component 11 was added thereto, and homogenized.

The UV-cut cream thus obtained was lightly spreadable and gave pellucid finish without stickiness and greasy touch.

(Example 15) O/W-Type UV-Cut Cream

TABLE 10

| | Components | % by mass |
|---|---|---|
| 1. | crosslinked dimethylpolysiloxane (*1) | 5.0 |
| 2. | cetyl isooctanate | 5.0 |
| 3. | octyl methoxycinnamate | 2.0 |
| 4. | titanium oxide/decamethyl-cyclopentasiloxane dispersion (*2) | 15.0 |
| 5. | polyether-modified silicone (*3) | 1.0 |
| 6. | polyether-modified silicone (*4) | 1.0 |
| 7. | acrylic amide-type mixture (*5) | 2.0 |
| 8. | propylene glycol | 5.0 |
| 9. | methyl cellulose (2% aqueous solution) (*6) | 1.0 |
| 10. | antiseptic | Dosage |
| 11. | perfume | Dosage |
| 12. | Water absorbing polymer particle 3 | 5.0 |
| 13. | water | Residue |

(*1) KSG-15 (trade name): manufactured by Shin-Etsu Chemical Co., Ltd.
(*2) SPD-T5 (trade name): manufactured by Shin-Etsu Chemical Co., Ltd.
(*3) KF-6013 (trade name): manufactured by Shin-Etsu Chemical Co., Ltd.
(*4) KF-6011 (trade name): manufactured by Shin-Etsu Chemical Co., Ltd.
(*5) SEPIGEL 305 (trade name); manufactured by SEPIC
(*6) METOLOSE SM-4000 (trade name): manufactured by Shin-Etsu Chemical Co., Ltd.

(Production Method)
A: components 5 to 9, 10, 12, and 13 were mixed.
B: components 1 to 3 were mixed and heated, and added to the mixture obtained by A, which was stirred and emulsified.
C: component 4 was added to the emulsion obtained by B, which was stirred and emulsified. Component 11 was added thereto, and homogenized.

The UV-cut cream thus obtained was lightly spreadable and gave pellucid finish without stickiness and greasy touch.

(Example 16) W/O-Type Milky Lotion

TABLE 11

| | Components | % by mass |
|---|---|---|
| 1. | crosslinked polyether-modified silicone (*1) | 5.0 |
| 2. | crossiinked dimethylpolysiloxane (*2) | 5.0 |
| 3. | polyether-modified silicone (*3) | 1.0 |
| 4. | dimethylpolysiloxane (6 mm$^2$/s (25° C.)) | 8.0 |
| 5. | decamethylcyclopentasiloxane | 13.0 |
| 6. | glyceryl trioctanoate | 5.0 |
| 7. | 1,3-butylene glycol | 6.0 |
| 8. | antiseptic | Dosage |
| 9. | perfume | Dosage |
| 10. | Water absorbing polymer particle 4 | 5.0 |
| 11. | water | Residue |

(*1) KSG-210 (trade name): manufactured by Shin-Etsu Chemical Co., Ltd.
(*2) KSG-15 (trade name): manufactured by Shin-Etsu Chemical Co., Ltd.
(*3) KF-6017 (trade name): manufactured by Shin-Etsu Chemical Co., Ltd.

(Production Method)
A: components 1 to 7 were mixed.
B: components 8 to 11 were mixed, and added to the mixture obtained by A, which was emulsified.

The milky lotion thus obtained was an W/O-type milky lotion that was lightly spreadable and had excellent adhesion feeling in use without stickiness.

(Example 17) Antiperspirant (Roll-On) Composition

TABLE 12

| | Components | % by mass |
|---|---|---|
| 1. | polyether-modified silicon (*1) | 0.5 |
| 2. | hydroxy-aluminum chloride | 3.0 |
| 3. | talc | 5.0 |
| 4. | ethyl alcohol | 15.0 |
| 5. | hydroxyethyl cellulose | 2.0 |
| 6. | Water absorbing polymer particle 5 | 5.0 |
| 7. | water | 69.5 |

(*1) KF-6011: manufactured by Shin-Etsu Chemical Co., Ltd.

(Production Method)

A: components 1 to 7 were mixed.

B: the mixture obtained by A was fed in a roll-on container.

The antiperspirant composition thus obtained gave light and smooth touch after it was dried without causing stickiness in application thereof, and was excellent in usability.

(Example 18) Shampoo

TABLE 13

| | Components | % by mass |
|---|---|---|
| 1. | sodium polyoxyethylene (EO:3) lauryl sulfate (30% aqueous solution) | 30.0 |
| 2. | lauryl sulfate diethanolamide | 4.0 |
| 3. | propylene glycol | 2.0 |
| 4. | antiseptic agent, colorant, perfume | Dosage |
| 5. | Water absorbing polymer particle 1 | 5.0 |
| 6. | water | Residue |

(Production Method)

Components 1 to 6 were mixed with a mixer.

The obtained shampoo gave smooth touch without causing stickiness in application thereof, and was excellent in usability.

As described above, the inventive cosmetic is capable of providing excellent usability such as lightly spreading and smooth touch, thereby making the skin have smooth and soft touch without causing stickiness or dullness in application thereof.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A water absorbing resin having a siloxane skeleton, being a copolymer comprising:

a structural unit derived from a polymerizable vinyl monomer (A) shown by the following general formula (1),

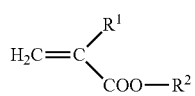

(1)

wherein, $R^1$ represents a hydrogen atom or a hydrocarbon group having 1 to 3 carbon atoms; $R^2$ represents a hydrocarbon group having 1 to 6 carbon atoms or a group shown by the following general formula (2); with the polymerizable vinyl monomer (A) optionally being a combination of the polymerizable vinyl monomers that differ in $R^2$;

$$-(CH_2)_a-(OC_2H_4)_b-(OC_3H_6)_c-OR^3 \quad (2)$$

wherein, "a" is an integer of 1 to 4, $0 \leq b \leq 30$, $0 \leq c \leq 30$, and $0 < b+c \leq 40$; $R^3$ represents a hydrogen atom or a hydrocarbon group having 1 to 4 carbon atoms;

a structural unit derived from a polymerizable vinyl monomer (B) shown by the following general formula (3),

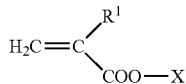

(3)

wherein, $R^1$ is as described above; a combination of a hydrogen atom and a sodium ion, wherein the molar ratio of the sodium ion/the hydrogen atom is $\geq 0.2$;

a structural unit derived from an organopolysiloxane (C) having polymerizable groups at the both terminals thereof shown by the following general formula (4),

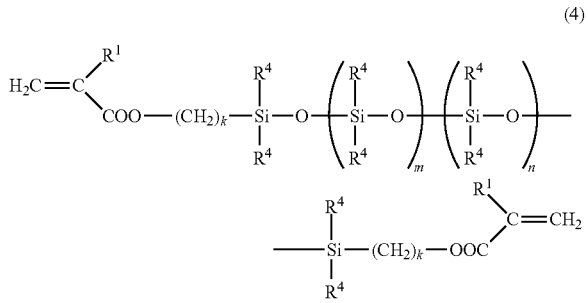

(4)

wherein, "k" is an integer of 1 to 4; $R^1$ is as described above; $R^4$ represents a hydrocarbon group having 1 to 8 carbon atoms; $R^5$ represents $R^4$ or a group shown by the general formula (2); and "m" and "n" are integers of $0 \leq m \leq 100$ and $0 \leq n \leq 20$ satisfying $0 \leq m+n \leq 100$; wherein the polymerizable vinyl monomer (A) and/or the organopolysiloxane (C) comprise $R^2$ representing a group shown by the general formula (2).

2. The water absorbing resin having a siloxane skeleton according to claim 1, wherein the water absorbing resin having a siloxane skeleton is a copolymer that contains 50 to 90% by mass of the structural unit derived from the polymerizable vinyl monomer (A), 10 to 50% by mass of the structural unit derived from the polymerizable vinyl monomer (B), and 2 to 30% by mass of the structural unit derived from the organopolysiloxane (C) in a ratio relative to the mass of the water absorbing resin.

3. The water absorbing resin having a siloxane skeleton according to claim 1, further comprising a structural unit derived from a polymerizable vinyl monomer (D) having an organopolysiloxane group shown by the following general formula (5),

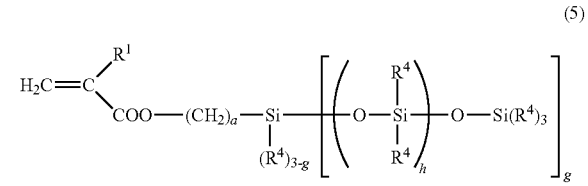

(5)

wherein, "a", $R^1$, and $R^4$ are as described above; "g" is an integer of 1 to 3, and "h" is an integer of 0 to 500 on average.

4. A cosmetic comprising 0.1 to 10% by mass of the water absorbing resin having a siloxane skeleton according to claim 1.

5. The cosmetic according to claim 4, further comprising an oil material (E) selected from the group consisting of silicone oils, hydrocarbon oils, ester oils, and glyceride oils.

6. The cosmetic according to claim 4, further comprising an alcohol (F) having 2 to 12 carbon atoms.

7. The cosmetic according to claim 4, further comprising a water-soluble or water-swellable polymer (G).

8. The cosmetic according to claim 4, further comprising powder and/or colorant as a component (H).

9. The cosmetic according to claim 8, wherein the component (H) contains polyethylene powder, polypropylene powder, spherical powder of silicone elastomer, spherical polymethylsilsesquioxane powder, spherical powder of silicone elastomer coated with polymethylsilsesquioxane, or polyurethane powder.

10. The cosmetic according to claim 4, further comprising a surfactant (I).

11. The cosmetic according to claim 10, wherein the surfactant (I) is selected from the group consisting of polyoxyalkylene-modified linear or branched organopolysiloxanes, polyglycerin-modified linear or branched organopolysiloxanes, and alkyl co-modified organopolysiloxanes thereof.

12. The cosmetic according to claim 4, further comprising a composition (J) composed of a liquid oil material and a crosslinked organopolysiloxane polymer other than the water absorbing resin having a siloxane skeleton.

13. The cosmetic according to claim 4, further comprising a composition (K) composed of a liquid oil material and a crosslinked organopolysiloxane polymer having a polyether group and/or a polyglycerin group other than the water absorbing resin having a siloxane skeleton.

14. The cosmetic according to claim 13, wherein the crosslinked organopolysiloxane polymer having a polyether group and/or a polyglycerin group is a crosslinked organopolysiloxane polymer prepared from methylhydrogenpolysiloxane grafted with a polyoxyethylene chain and/or methylhydrogenpolysiloxane grafted with a polyglycerin chain.

15. The cosmetic according to claim 4, further comprising a silicone resin (L) selected from the group consisting of a silicone network compound containing an $SiO_2$ unit and/or an $RSiO_{3/2}$ unit (R represents an alkyl group), and a linear acryl/silicone graft- or block-copolymer.

16. The cosmetic according to claim 15, wherein the silicone network compound is at least one resin selected from the group consisting of resins composed of an $R_3SiO_{1/2}$ unit and an $SiO_2$ unit; resins composed of an $R_3SiO_{1/2}$ unit, an $R_2SiO$ unit, and an $SiO_2$ unit; resins composed of an $R_3SiO_{1/2}$ unit and an $RSiO_{3/2}$ unit; resins composed of an $R_3SiO_{1/2}$ unit, an $R_2SiO$ unit, and an $RSiO_{3/2}$ unit; and resins composed of an $R_3SiO_{1/2}$ unit, an $R_2SiO$ unit, an $RSiO_{3/2}$ unit, and an $SiO_2$ unit.

17. The cosmetic according to claim 16, wherein the silicone network compound contains at least one moiety selected from the group consisting of pyrrolidone moieties, long chain alkyl moieties, polyoxyalkylene moieties, fluoroalkyl moieties, and amino moieties.

18. The cosmetic according to claim 15, wherein the linear acryl/silicone graft- or block-copolymer contains at least one organic group selected from the group consisting of pyrrolidone groups, long chain alkyl groups, polyoxyalkylene groups, fluoroalkyl groups, and anionic carboxy groups.

19. The cosmetic according to claim 4, further comprising an ultraviolet light protective component (M).

20. The cosmetic according to claim 4, wherein the cosmetic is an aqueous cosmetic selected from the group consisting of skincare cosmetics, hair cosmetics, antiperspirants, makeup cosmetics, and ultraviolet light protective cosmetics.

21. The cosmetic according to claim 20, wherein the cosmetic is in a form selected from liquid, emulsion, cream, solid, paste, gel, and mousse.

22. The cosmetic according to claim 21, wherein the cosmetic is an O/W-type cream, foundation, shampoo, or rinse.

\* \* \* \* \*